(12) United States Patent
Stubber

(10) Patent No.: US 9,033,943 B2
(45) Date of Patent: May 19, 2015

(54) WOUND DRAINAGE CONTROL APPARATUS

(75) Inventor: Raymond Lawrence Stubber, Sorrento (AU)

(73) Assignee: Research Medical Pty. Ltd., Sorrento (AU)

( * ) Notice: Subject to any disclaimer, the term of this patent is extended or adjusted under 35 U.S.C. 154(b) by 0 days.

(21) Appl. No.: 13/806,903

(22) PCT Filed: May 10, 2011

(86) PCT No.: PCT/AU2011/000533
§ 371 (c)(1),
(2), (4) Date: Dec. 26, 2012

(87) PCT Pub. No.: WO2012/000014
PCT Pub. Date: Jan. 5, 2012

(65) Prior Publication Data
US 2013/0102980 A1 Apr. 25, 2013

(30) Foreign Application Priority Data
Jun. 29, 2010 (AU) ................................ 2010902868

(51) Int. Cl.
*A61M 1/00* (2006.01)
(52) U.S. Cl.
CPC ........... *A61M 1/0031* (2013.01); *A61M 1/0001* (2013.01); *A61M 1/0088* (2013.01)
(58) Field of Classification Search
USPC ...................................... 604/9, 317, 319, 320
See application file for complete search history.

(56) References Cited

U.S. PATENT DOCUMENTS

| 4,540,400 A | 9/1985 | Hooven |
| 4,769,002 A * | 9/1988 | Hooven ............................ 604/9 |
| 5,643,195 A * | 7/1997 | Drevet et al. ...................... 604/9 |
| 5,944,703 A | 8/1999 | Dixon et al. |
| 6,554,327 B1 * | 4/2003 | Riley ............................ 292/152 |
| 6,702,249 B2 | 3/2004 | Ito |
| 7,422,566 B2 * | 9/2008 | Miethke ............................ 604/9 |
| 2010/0010415 A1 * | 1/2010 | McCusker et al. ................ 604/9 |

OTHER PUBLICATIONS

International Search Report for PCT/AU2011/000533, mailed Jun. 24, 2011; ISA/AU.

* cited by examiner

*Primary Examiner* — Leslie Deak
*Assistant Examiner* — Kai Weng
(74) *Attorney, Agent, or Firm* — Harness, Dickey & Pierce, PLC

(57) ABSTRACT

A wound drainage device flow regulator for controlling fluid flow from a wound to a container. The regulator provides selective communication between a conduit and the container. The device includes a valve for communication between the conduit and the container in response to a level of vacuum in the conduit below a selected value. The valve has a diaphragm exposed to atmospheric pressure on one side and to the level of vacuum in the conduit on the other side. A force is applied to the diaphragm in opposition to atmospheric pressure. The difference between the force applied and the force generated by atmospheric pressure provides a control force required to be applied by the level of vacuum in the conduit to close the valve to interrupt communication between container and conduit. A lock mechanism locks the adjustable force mechanism at a desired adjustment corresponding to a desired level of vacuum.

16 Claims, 8 Drawing Sheets

WOUND DRAINAGE CONTROL APPARATUS

CROSS-REFERENCE TO RELATED APPLICATIONS

This application is a 371 U.S. National Stage of International Application No. PCT/AU2011/000533, filed on May 10, 2011, which claims priority to Australian Patent Application No. 2010902868, filed on Jun. 29, 2010. The contents of the above applications are incorporated herein by reference in their entirety.

FIELD OF THE INVENTION

This invention relates to control of closed wound drainage where sub-atmospheric pressure (partial vacuum) is employed to assist the drainage. The function of wound drainage is to promote rapid and efficient healing of post-operative wounds.

BACKGROUND OF THE INVENTION

A wide range of equipment has been proposed to assist in the draining of fluid from wounds, particularly wounds resulting from surgery or accidents. One type of known construction employs a bellows type container that can be reduced in volume against the pressure of internal springs or by the force of deformation of the container material to provide a vacuum source.

These types of construction exhibit several major limitations one being that to achieve the desired level of vacuum, the container must have a high degree of resilience to develop a vacuum of the order of several pounds per square inch. This is somewhat impractical in terms of cost effective manufacture and it is not possible to effectively control or maintain the desired vacuum level for efficient drainage. Further, as only a small degree of vacuum can be created, it dissipates rapidly as the container fills with fluid. Also, it is normally very difficult, if not impossible, to monitor accurately the rate at which the fluid is collected.

Another known type of equipment for the extraction and collection of wound fluid employs a disposable container connected to a re-useable electronically driven pump, and thus require elaborate and expensive electronics, a pump and rechargeable batteries or a power supply. The inherent complexities of this type of device entails significant additional cost for initial purchase and for maintenance of the pump and controller. While the fluid containers are disposable, special provisions must be made to ensure that the non-disposable components, such as the pump assembly, are protected from contamination by the drained wound fluid.

Yet a further known type of wound fluid collector is that employing a pre-evacuated container which use volatile liquids such as pentane and hexane to achieve the required level of vacuum. However these do not provide a capability to vary or otherwise control the level of vacuum, and if a leak occurs which dissipates the vacuum there is no ability to re-establish the vacuum. These systems often operate at a higher degree of vacuum than is ideally desired for optimum drainage in many situations.

There is a variant of this latter form of wound fluid collector which use an elaborate, separate, non-adjustable regulator of the flexible throttled tube type which can be attached to the drain bottle. This does help to avoid an overly strong suction, but still has the other shortcomings of the non-regulated system and additionally there is the substantial added cost of the regulator, which cannot be re-used for another patient, as the regulator becomes contaminated by the drained wound fluids during use.

The present applicant has previously proposed a flow control valve to, in use, selectively provide communication between the conduit and container, said valve means being adopted to establish communication between the conduit and the container in response to the existence of a level of vacuum in said conduit below a selected value. Such a device has been proposed in the present applicant's prior international patent application PCT/AU95/00674 (published as WO 96/11031) and granted in the United States of America as U.S. Pat. No. 5,944,703 and in Europe as EP 0783339, the contents of both of which are incorporated herein in their entirety. Embodiments of the device disclosed therein incorporate a compliant element, attached to a regulator valve, which compliant element is induced to flex by rotation against a circular ramp. The degree of flex induced is related to the degree of rotation, and can be read against a calibrated scale. The upward force resulting from the flexion of the compliant member moves the regulator valve, breaking the seal of the valve seat and allowing fluid to be drawn through a spigot tube into a drain container, thereby lowering the pressure in the area below the regulator valve, and through the orifice, equally lowering the pressure in the connecting tube and the drain tube. The magnitude of force applied by the compliant element is selectively adjustable by a rotational movement of the compliant element. The higher the force applied by the compliant element, the higher the level of vacuum maintained in the tube. Whilst such a device has been found to be efficacious in improving flow control, it has been found that under some circumstances the valve may be accidentally or unintentionally incorrectly adjusted, thereby causing an incorrect under or over setting of vacuum control between the wound drainage conduit and the container.

Improper setting can result in either insufficient drainage from the wound due to low vacuum, resulting in build up of fluid in the wound and increasing risk of infection, or, if incorrectly set to a high vacuum, causing discomfort to the patient. It has been realised that in such a device as disclosed in U.S. Pat. No. 5,944,703 and EP 0783339, the incorrect adjustment or setting may occur due to a patient or other person accidentally, unintentionally or absentmindedly rotating the compliant member. Also, another person, such as a carer or medical staff, may accidentally or un-intentionally rotate the compliant member when attending to personal needs of the patient, such as when adjusting the patient's clothing/bedding.

With the aforementioned in mind, it is desirable of the present invention to provide an improved apparatus for controlling closed wound drainage especially in regard to a avoiding incorrect flow control setting.

SUMMARY OF THE INVENTION

There is provided according to at least one form of the present invention a wound drainage device flow control apparatus, the wound drainage device for withdrawing fluid from a wound comprising a conduit to be connected at one end to a wound to receive fluid from the wound and to deliver said fluid to a container, the flow control apparatus including a valve to, in use, selectively provide communication between the conduit and container, said valve arranged to establish communication between the conduit and the container in response to the existence of a level of vacuum in said conduit below a selected value, the valve including a diaphragm exposed to atmospheric pressure on one side and to the level of vacuum in the conduit on the other side, and an adjustable force means arranged to apply a force to the diaphragm in opposition to the atmospheric pressure, the valve further including a lock mechanism to set the adjustable force means at a selected position corresponding to a desired level of vacuum.

Thus, the lock prevents accidental or inadvertent adjustment of the valve. Also, in the case of a releasable lock, a user is caused to positively consider that they are releasing the lock and therefore what or why adjustment is required, thereby adding a safety check.

In use, a difference between the force applied by the adjustable force means and the force generated by the atmospheric pressure provides a control force required to be applied by the level of vacuum in the conduit to close the valve means to interrupt communication between the container and the conduit, and consequently the level of vacuum existing to promote withdrawal of fluid from the wound.

Conveniently, the valve may be adjustable to respond to a level of vacuum between zero to a chosen maximum degree of vacuum thereby enabling the level of vacuum in the conduit to be adjusted to suit the prevailing wound condition.

Advantageously, the lock may be releasable and re-setable, or may be fixed once employed. A releasable lock can provide subsequent re-adjustment of the valve i.e. is re-setable. A fixed lock may be employed as a one off lock that once set is not further adjustable. The releasable lock may be user releasable with or without an additional tool, such as a pin, key, token or other release initiator.

In one or more embodiments, the lock may include one or more latches, such as a slide or pivot latch. For example, the lock may include a slidable latch arranged to engage with one or more lock points of the adjustable force means. The slidable latch may, once engaged with the one or more lock points may be releasable or may be fixed once locked in position. A releasable form of the latch may be provided through an interference or friction fit with the adjustable force means, or may include a positive catch arrangement whereby release force on the catch allows the latch to be released. The positive catch arrangement may include one or more resilient members arranged to positively engage with corresponding portions of the adjustable force means, and applying pressure to the resilient member(s) releases the latch from engagement with the adjustable force means.

The adjustable force means may include a rotatable member. Such a rotatable member may include one or more engagement portions around a periphery thereof. The lock may engage with one or more engagement portions at a selected position of rotation of the rotatable member.

Alternatively, or in addition, the rotatable member may be positively retained at a desired position by a ratchet mechanism providing a releasable lock. This may be provided by one or more ratchet members engaging into one or more respective ratchet recesses or teeth. The ratchet member(s) may be provided on the adjustable force means and the ratchet recess(es) or teeth on a corresponding portion of the valve fixed relative to the adjustable force means. For example, in the case of a rotatable member providing the adjustable force means, the rotatable member may have a series of ratchet teeth or recesses around at least a part of a periphery thereof, these ratchet teeth or recesses arranged to selectively engage with a resilient member on a fixed portion of the valve, such as a resilient projection on a valve body or valve cover.

The invention will be more readily understood from the following description of one practical arrangement of the wound drainage system and apparatus as illustrated in the accompanying drawings.

DETAILED DESCRIPTION OF THE EMBODIMENT

Figure 1:
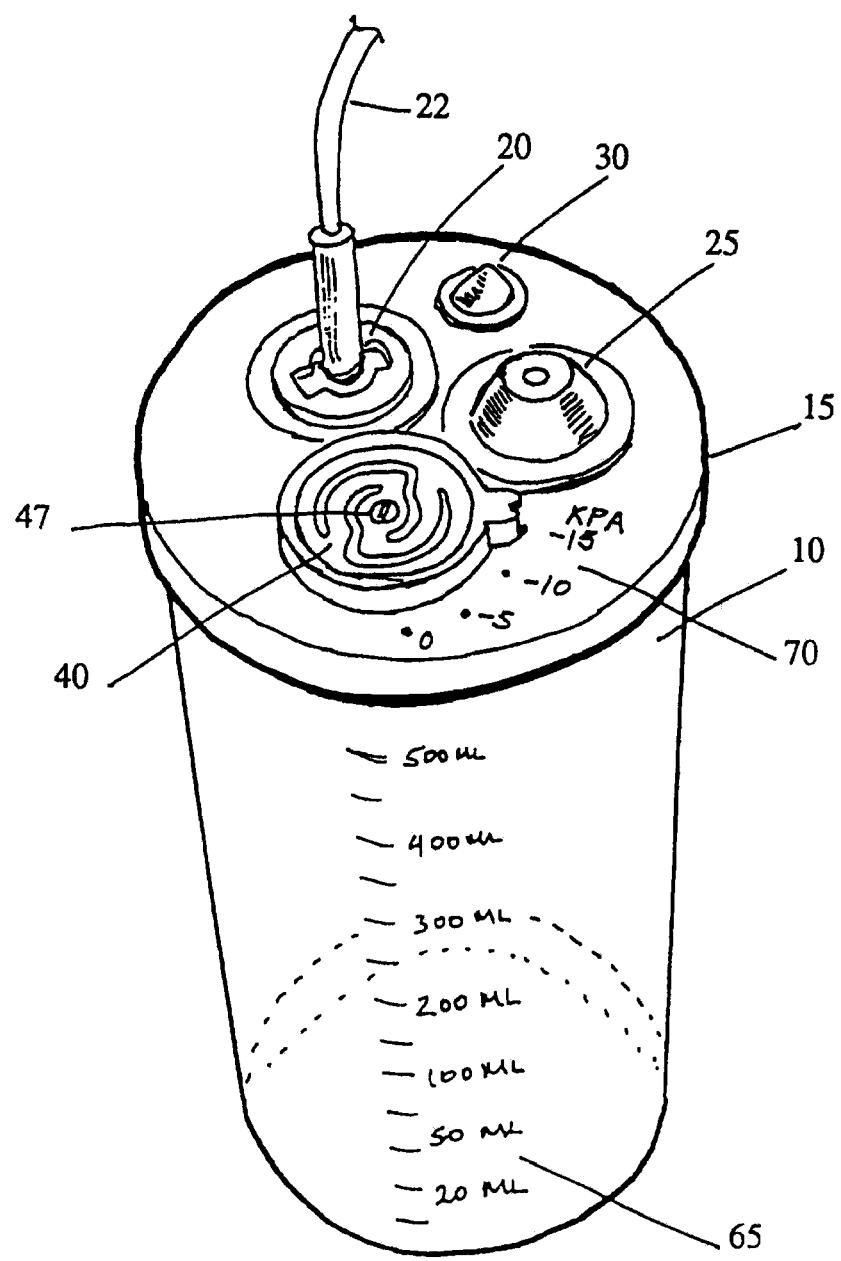
FIG. 1 is an isometric view of an overall configuration of a wound draining device.
Figure 2:
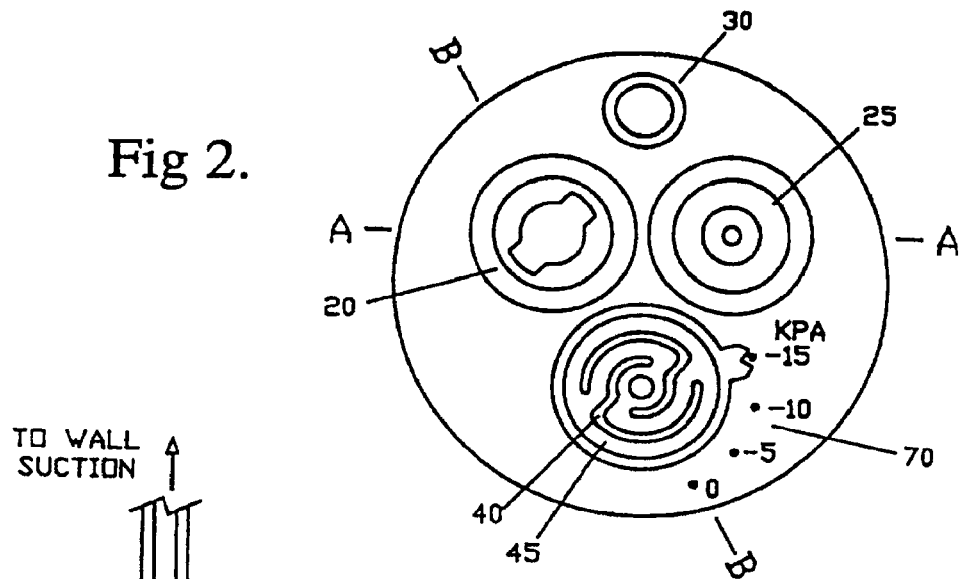
FIG. 2 is a plan view of the top of the draining device in FIG. 1.

A drainage system includes a drainage container 10 with a cap 15 in which the functional components of the system are incorporated. The functional components include a drain tube 22, the free end (not shown) of which in use communicates with the wound site in the known conventional manner, is connected at the other end by a bayonet type fitting 20 to the cap 15 of the container 10 and incorporates a check valve 35 that will not permit flow outward from the container 10 into the tube 22.

The tube 50 within the container 10 extends from the check valve 35 to the underside of the regulator valve 40. The spigot 25, incorporating a further check valve 26, is provided for connection to a conventional in situ hospital vacuum system, thereby enabling evacuation of the drainage container 10. The resilient cone 30 functions as a diaphragm to be defected into the container 10 to visually indicate the presence of at least partial vacuum in the container 10.

Figure 4:
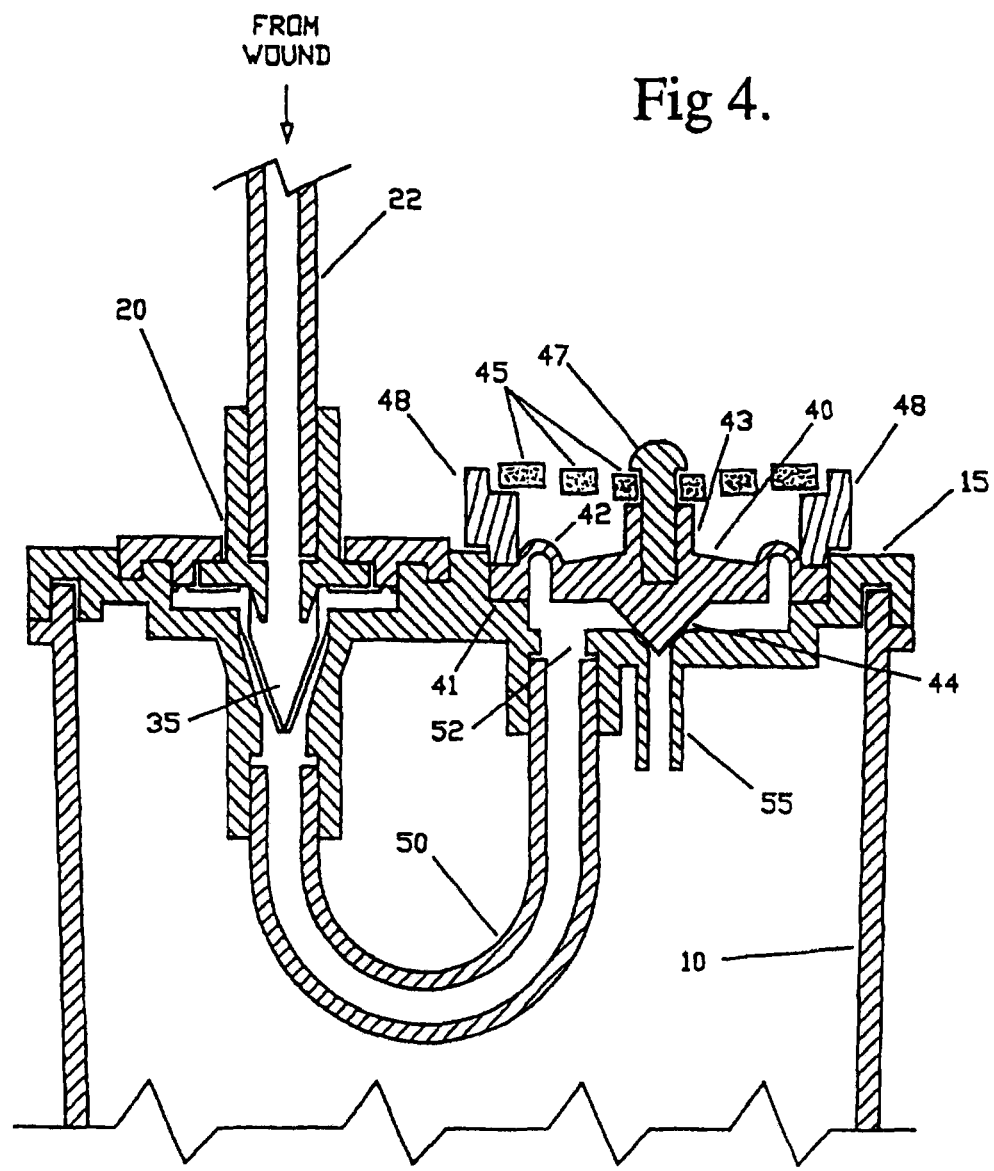
FIG. 4 is a partial section on line B-B of FIG. 2.

Referring to FIG. 4, the regulator valve 40 consists of a moulded elastomer disc sealably secured at the perimeter 41 thereof to the cap, and has a concentric annular compliant section 42 a threaded boss 43 at the centre of the upper face, and a central valve section 44 on the lower face. In the free position of the regulator valve 40 the valve section 44 will engage the seat 63 in the upper end of the drain tube 50 to close the tube. Above the regulator valve 40 is a rotatable compliant or resilient element 45 which when rotated will adjust the force applied to the regulator 40, in opposition to atmospheric pressure applied externally thereto.

The magnitude of force applied by the compliant element 45 is selectively adjustable by a rotational movement of the compliant element 45 in the peripheral support 48 thereof. The degree of rotation is indicated by markings 70, resulting in an indication of the up force applied to the regulator 40. The higher the force applied by the compliant element 45, the higher the level of vacuum maintained in the tube 50. This level can be further varied through the use of different grades of compliant component for different applications of the drainage system.

When wound fluid is aspirated through the tube 50 to the underside of the regulator valve 40, it is then vented through the spigot 55 into the interior of the drain container 10. The drain container has an inverted conical base 60, which allows for an expanded vertical scale of the level indicator 65 for more accurate measurement of the initial flow of wound fluid. The inverted conical shape is also advantageous in that it improves the resistance of the container to deformation due to the presence of vacuum therein.

It is well established from clinical practice that healing of post-operative wounds is assisted by proper drainage of excess fluid from within the wound site. The ideal degree of suction to be applied will vary from case to case and from time to time during the healing process. However, it can be said that the degree of suction is generally agreed to desirable lie in the range between zero and 15 kPa below atmospheric pressure.

Wall mounted reticulated vacuum systems commonly provided in hospitals are typically set between 65 and 80 kPa below atmospheric pressure (101.3 kPa), which is much too strong a suction to be used for continuous wound drainage.

The level of vacuum to be applied to the wound site by the presently proposed system is controllable through the regulator valve 40, which controls the pressure level in the wound drain tube 22. The pressure in the drainage container 10 and at the point where the spigot tube 55 meets the valve seat 63 will typically be around 70 kPa below atmospheric, immediately after evacuation by the hospital reticulated vacuum system. As the regulator valve 40 in this state is closed, no fluid can flow until there is an upward force applied to the regulator valve 40.

If gravity drainage without suction assistance is required, the upward force applied to the regulator valve can be set to zero. Independent of the degree of vacuum in the container 10, any pressure rise in the drain line 22, due to newly produced wound fluid, will be sufficient to crack the valve seal 44 and allow fluid to flow into the container through the drain spigot tube 55.

Where suction assistance is required, this is achieved by the compliant element 45, secured to the boss 43 of the regulator valve 40 by a screw 47, which is induced to flex by rotation against a circular ramp 48. The degree of flex induced is related to the degree of rotation, and can be read against the calibrated scale 70. The upward force resulting from the flexion of the compliant member 45 cracks the regulator valve 40, breaking the seal of the valve seat 44 and allowing fluid to be drawn through the spigot tube 55 into the drain container 10, thereby lowering the pressure in the area below the regulator valve, and through the orifice 52, equally lowering the pressure in the connecting tube 50 and the drain tube 22.

As fluid is passed into the drainage container 10, the pressure will reduce until a level is reached where the downward force on the lower surface of the regulator valve 40 opposing the upward flexion force applied by the compliant element 45, reaches a point of equilibrium. The regulator valve 40 will then return to its closed position. The regulator valve needs only to move small fractions of a millimeter in the transition between closed and open.

The state of equilibrium where the valve is closed can only be disturbed by either changing the upward force applied to the regulator valve 40 by the compliant element 45, thereby requiring an increased level of vacuum in the system to restore equilibrium, or by the production of a flow of wound fluid into the drain tube 22. The added volume of fluid will dissipate the level of vacuum in the drain line 22 and connecting tube 50, hence lowering the downward force on the regulator valve 40. This in turn will allow flow of wound fluid into the drain container 10, thereby increasing the level of vacuum until equilibrium is again restored.

As fluid flows into the drain container 10, the level of vacuum therein will gradually dissipate. A container of 600 mls, evacuated to minus 75 kPa, will, after draining 400 mls of wound fluid will fall to minus 10 kPa, and upon draining 450 mls the vacuum will completely dissipated.

The regulated level of vacuum in the drain line 22 is controlled by the effective size of the regulator disc 42 measured at the centre line of the annular compliant element 45 and the consequent force applied from a given pressure differential, balanced against the degree of force applied by the compliant element 45. The regulated pressure will not be adversely influenced by variation in the level of vacuum in the drain container 10 if the cross sectional area of the spigot tube 55 is kept to less than 2% of the effective area of the regulator disc 42.

Figure 5:
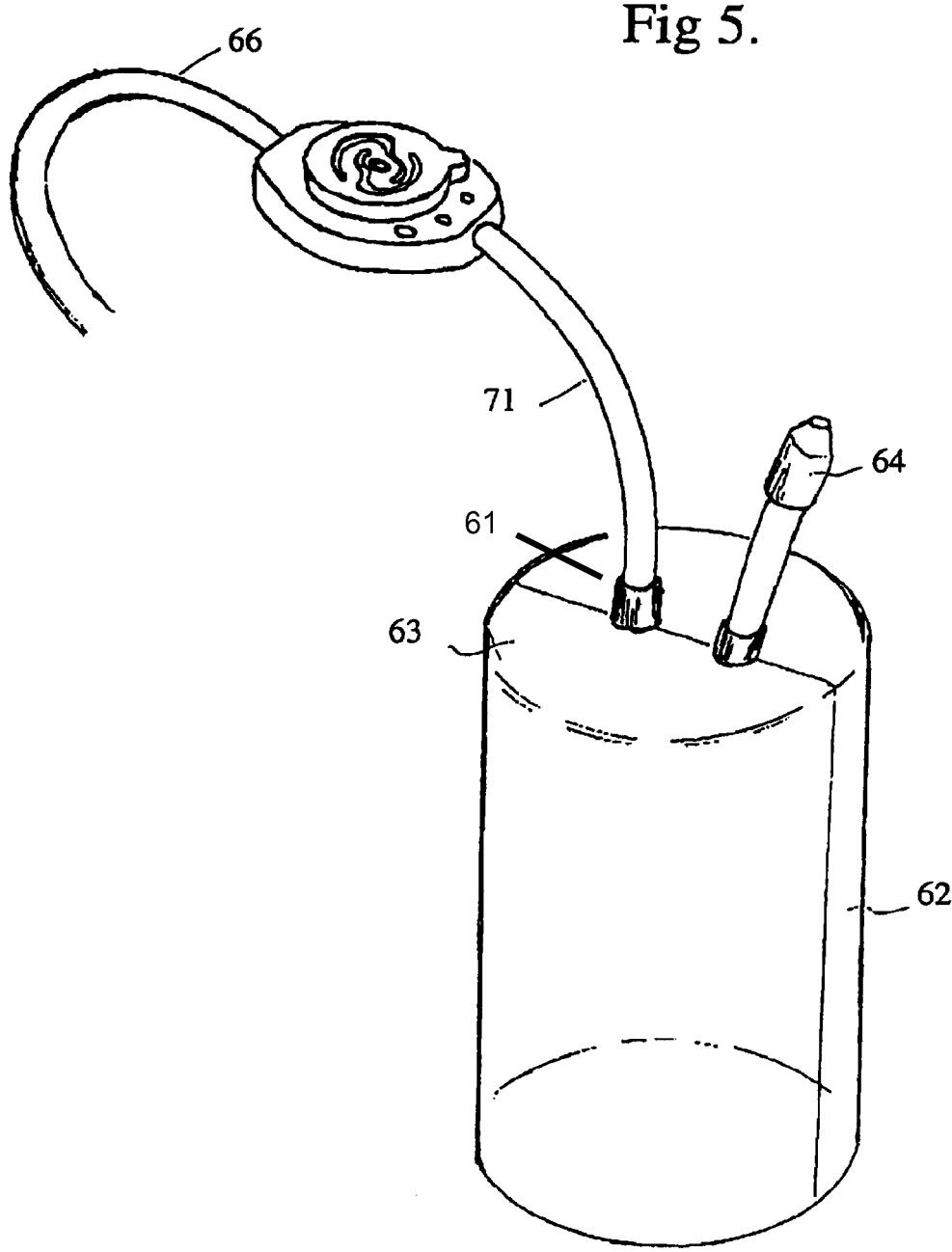
FIG. 5 is an isometric view of the overall configuration of an alternative arrangement of the draining device showing the regulator device within the drain line.
Figure 6:
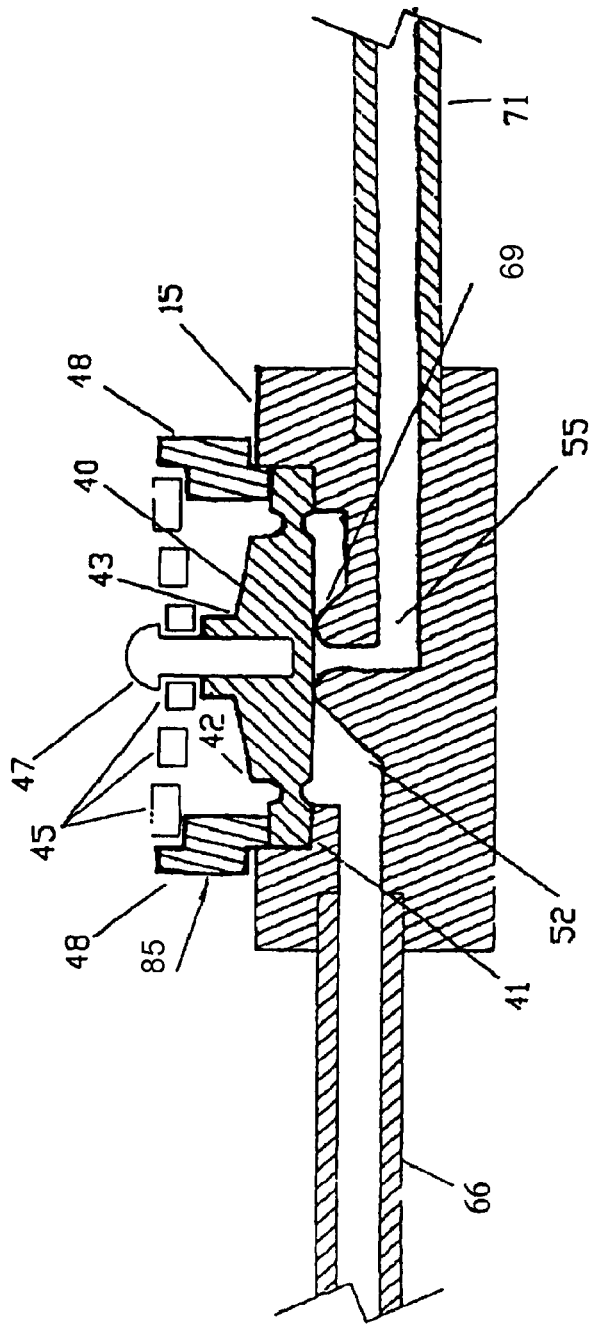
FIG. 6 is a sectional view of the regulator valve shown in FIG. 5.

There is shown in FIGS. 5 and 6 an alternative form of the wound drainage system wherein the regulator valve is constructed independent of the container wherein the wound fluid is collected. By separating the regulator valve from the container, the container can be of a simplified construction that can be effectively sterilised and therefore be re-used numerous times. This is a substantial commercial advantage compared with the integrally constructed container and regulator valve unit described with reference to FIGS. 1 to 4, which cannot be effectively sterilised, and hence must be totally discarded after a single use.

Figure 3:
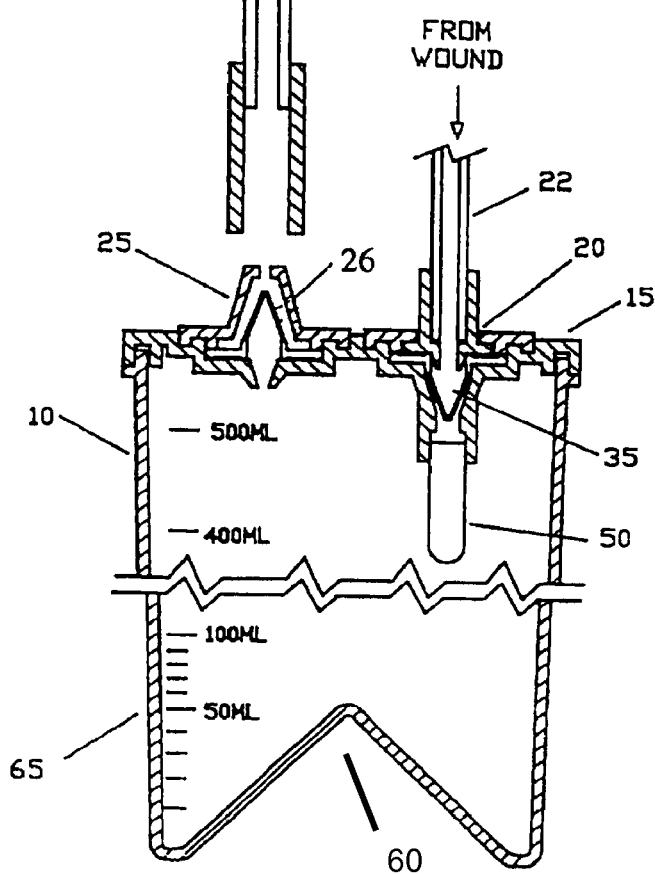
FIG. 3 is a section on line B-B of FIG. 2.

As seen in FIG. 5, the container 62 is of a simple cylindrical form with a removable closure 61, and may have an inverted conical base as shown in FIG. 3 in relation to the container 60. The container cap 63 is removable for discarding of the fluid collected therein and for sterilisation between successive uses. The coupling 64 provided in the cap 63 is connectable to the hospital reticulated vacuum system to enable initial establishment of the required level of vacuum in the container.

The independent regulator 65 is connected to the container 62 by the tube 71 and to the wound by a conventional wound drainage tube portion of which is shown at 66.

The construction and operation of the regulator 65 is substantially the same as the regulator 40 previously described. The regulator disc 42, compliance element 45 and screw 47, and the operation and adjustment thereof, are each identical to that previously described with reference to FIGS. 3 and 4, and have therefore been identified by the same reference numeral. The description thereof will not be repeated here. The differences from the regulator 40 reside in the wound fluid drain tube 66 being received in sealed relation in the cavity 69 to communicate with the cavity 52 immediately upstream of the valve 44. Also the passage 55, downstream of the valve 44, communicates directly with the transfer tube 71 via which wound fluid is transferred to an independent container (not shown) but would basically be the same as the container 10, but without the regulator valve incorporated therein.

This construction employing separate regulator valve and fluid collection container, providing the ability for multiple use of the container significantly improves the economics of the complete would drainage unit.

In the regulator valve described with reference to FIGS. 2, 3 and 4 or FIGS. 5 and 6, the compliant member 45 is in the form of a disk which is rotated against a circular ramp to vary the degree of flexion induced, thus exerting an upward force on the regulator valve 40. The same functional effect could also be achieved by employing other means such as:

a compliant beam secured to the cap 48 at one end, and to the regulator valve 40 at the other, with a central screw or ramp device to lift the beam's centre point, thereby applying a controlled upward force to the regulator valve; a compliant beam secured to the regulator valve at one end, with a fulcrum in the centre and a screw or ramp device to press down on the other end, which would also apply a controlled upward force to the regulator valve; a tension spring, one end attached to the upper side of the regulator valve, the other to an adjustably moveable anchor point, allowing variable tension force to be generated in the spring, thus applying a controlled upward force to the regulator valve.

The materials envisioned for the construction of the invention would favour appropriate grades of mouldable plastics, but need not be limited to these. Other materials such as glass, metals and rubber could equally be employed as and where cost and performance dictated.

Figure 7:
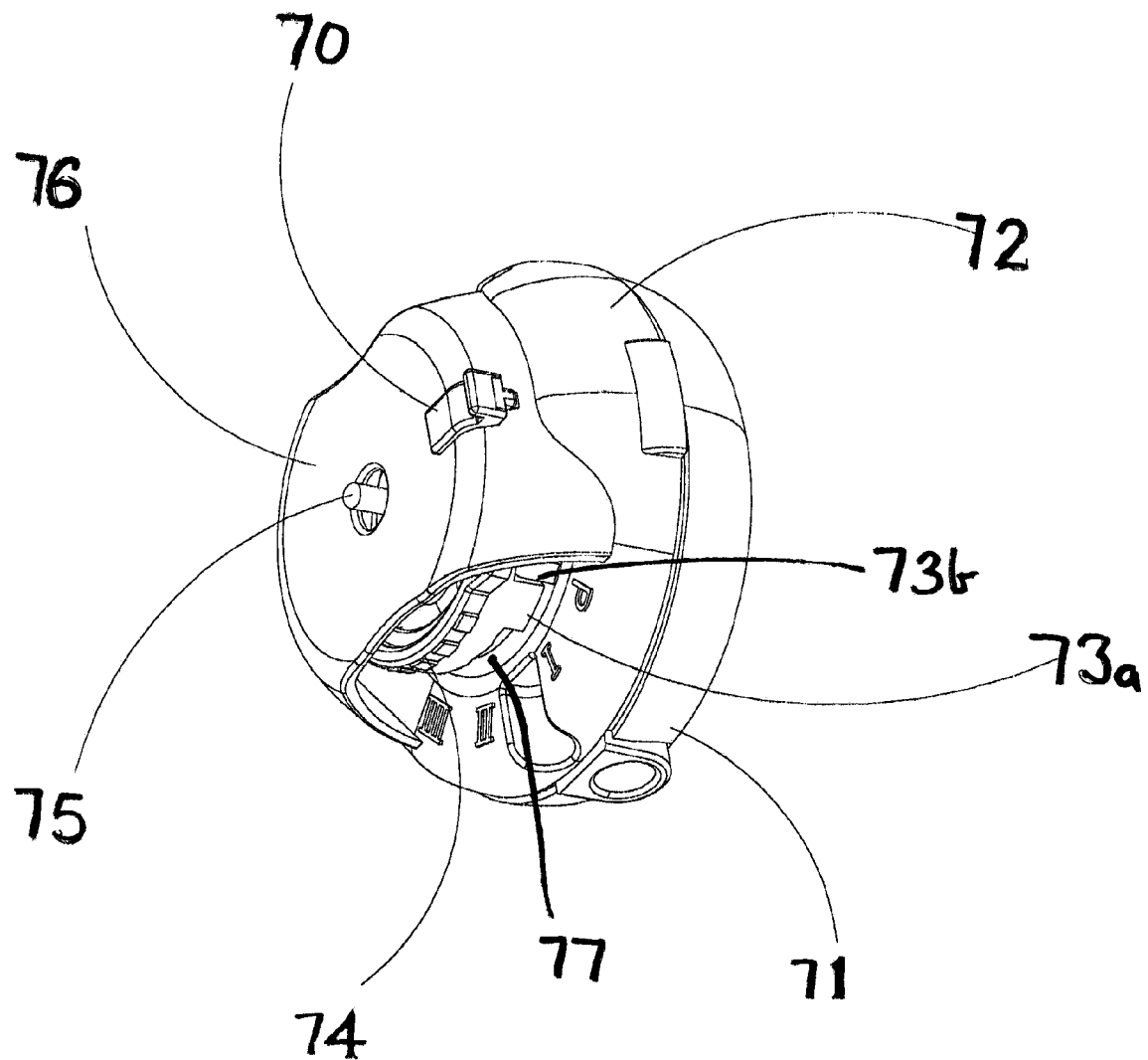
FIG. 7 is a perspective view of an overall configuration of a flow control apparatus according to an embodiment of the present invention.

FIG. 7 shows a regulator valve with lock mechanism according to an embodiment of the present invention. The lock mechanism includes a lock member 70 slidably retained in a cover 76. The lock member is arranged to slide into engagement with one or more respective engagement portions (see FIGS. 8a and 8b) on an adjuster, in this instance a rotatable adjuster 74, such as a compliant member described above. The adjuster is arranged to adjust force applied to a regulator valve resilient member 75 controlling fluid flow through the apparatus. As described in relation to the other figures, the adjuster (compliant member) is rotated in engagement with a ramp 77 to vary the degree of flexion induced, thus exerting an upward force on the regulator valve 75 to set a required vacuum control. A stop limiter 73 can be provided such that a minimum and/or maximum flow control can be set. In the embodiment shown, the stop limiter 73a is provided by a stop member abutting a fixed member 73b on the upper valve body 72. Predetermined vacuum levels my be provided, such as a P, I, II and III shown on the apparatus in FIG. 7. With the apparatus adjusted to a required vacuum level by rotating the compliant member, the lock mechanism can be engaged to ensure that the rotatable compliant member does not further rotate and cause the apparatus to be out of adjustment unless the lock mechanism is released.

In the embodiment shown in FIG. 7, the lock mechanism slides inward with respect to the cover 76 to engage with the adjuster 74. To release the lock, the lock member 70 is forced partially outward relative to the cover. This causes the lock member to disengage from the adjuster and allow adjustment of the compliant member. The lock can thereafter be re-engaged at the newly desired vacuum setting. It will be appreciated that the flow control apparatus (e.g. the regulator valve) can be adjusted and locked closed so that the valve seals the flow passage between the drainage conduit and the drainage container. The container can be removed and a fresh container connected in its place. The valve can thereafter be reopened and set and locked at a desired vacuum level. The lock can therefore assist in ensuring that the valve is not opened whilst there is no container attached.

Figure 8A:
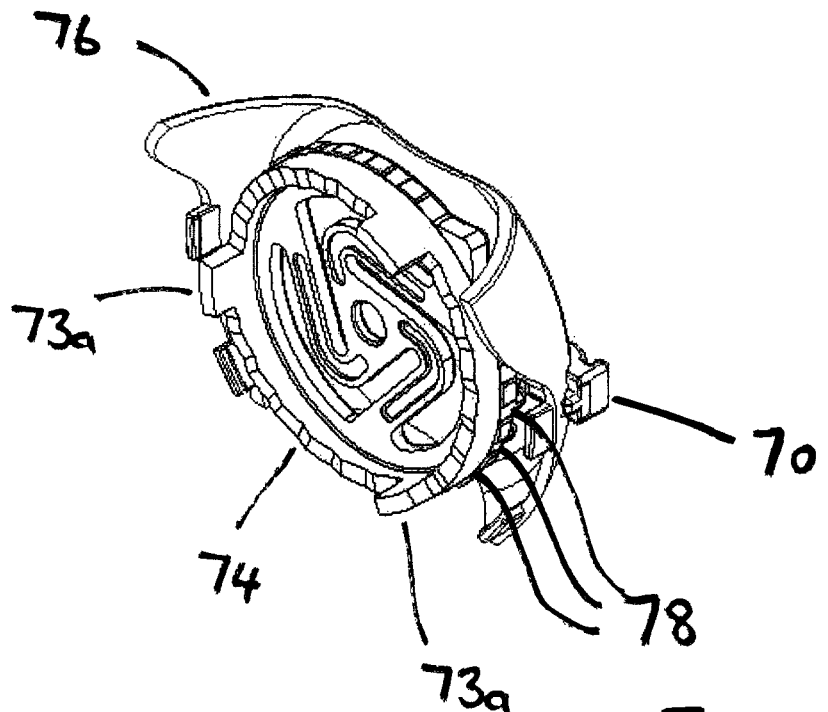
FIGS. 8a and 8b show partial exploded views of a flow control valve with a lock mechanism and associated components according to an embodiment of the present invention.
Figure 8B:
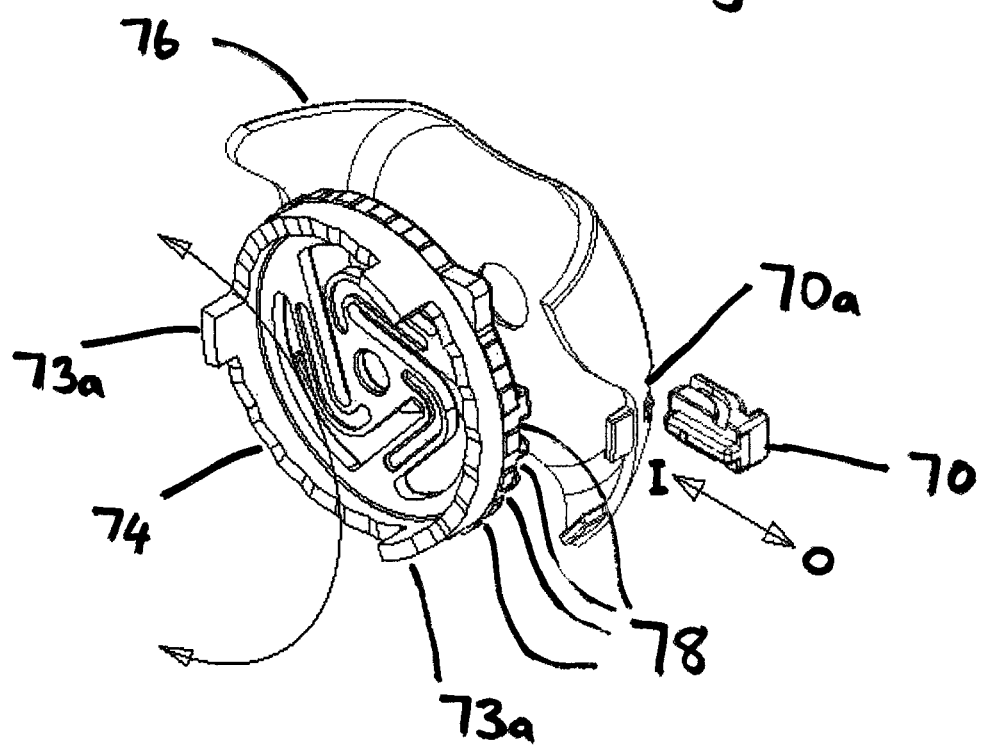

FIGS. 8a and 8b show partial exploded views of the flow control apparatus of FIG. 7. The lock member 70 is slidably retained in a slot 70a in the cover 76. The lock member 70 is arranged to slide inward (I) for locking and outward (O) for release. It will be appreciated that the lock may be a single use i.e. not releasable once engaged or releasable. If not releasable, there is provided a one way locking mechanism, such as a resilient lug or projection on the lock member or reciprocally on the cover that prevents the lock member being moved outward relative to the cover. The adjustable force means eg the adjuster or compliant member, includes a number of lock member engagement portions 78, being in this embodiment a series of recesses around the periphery of the complaint member. It will, however, be appreciated that other re-engagement means may be provided, such as apertures or projections and the lock member provided with one or more complimentary engagement portions.

In use, the adjuster 74 is rotated to a required position to set a desired vacuum level. The projections 73a contact a ramp on the valve upper body 72 (see FIG. 7) to raise or lower the adjuster dependent on the direction of rotation, as previously described. Once a desired position is chosen, the lock is engaged by sliding the lock member 70 into engagement with a corresponding lock member engagement portion 78. To release this particular lock, the lock member is slid outwards to release the lock member 70 from engagement with the corresponding lock member engagement portion 78.

Figure 9:
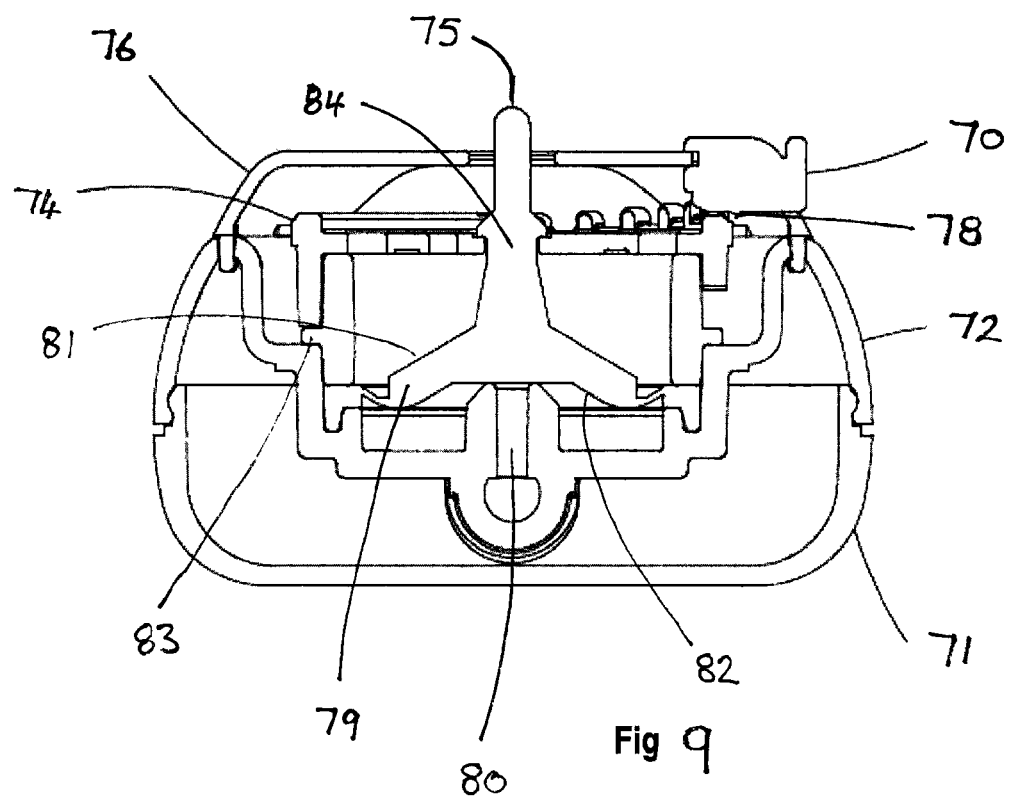
FIG. 9 shows a sectional view of a flow control valve of FIG. 7.

FIG. 9 shows a sectional view of an embodiment of the flow control valve. The valve body has bottom 71 and top sections 72 housing a diaphragm 79 of the regulator valve 75. The diaphragm is made of a resilient material, such as silicon rubber. In use, the diaphragm provides variable sealing of the port 80 to control flow of fluid drained from a wound to a container, the control being dictated by ambient pressure acting on the top surface 81 and vacuum from the container acting on the underside surface 82 of the valve compared with an upward lifting force applied by the adjuster 74. The adjuster, in this embodiment, rotates in contact with a ramp 83 causing the adjuster to apply an upward force to the central spigot 84 of the flow control valve. Adjustment can be set by causing the lock member 70 to engage with one or more complimentary engaging points 78 on the adjuster. The lock member is carried in a cover 76 of the flow control device. However, other locking mechanisms and arrangements are considered to fall within the scope of the present invention. For example, locking may be achieved by a locking pin and aperture arrangement, whereby a locking pin is inserted through an aperture in the adjuster preventing further movement of the adjuster. It will be appreciated that the aforementioned embodiments should not be taken to limit the breadth of the present invention.

The invention claimed is:

1. A wound drainage device flow control apparatus, the wound drainage device for withdrawing fluid from a wound comprising a conduit to be connected at one end to a wound to receive fluid from the wound and to deliver said fluid to a container, the flow control apparatus comprising a valve arranged to establish communication between the conduit and the container in response to a level of vacuum in said conduit below a selected value, the valve including a diaphragm exposed to atmospheric pressure on one side and to the level of vacuum in the conduit on the other side, and an adjustable force means arranged to apply a force to the diaphragm in opposition to the atmospheric pressure, the difference between the force applied by the adjustable force means and the force generated by the atmospheric pressure providing a control force required to be applied by the level of vacuum in the conduit to close the valve to interrupt communication between the container and the conduit, and a lock mechanism arranged to lock the adjustable force means at a desired adjustment corresponding to a desired level of vacuum, whereby the lock mechanism includes a slidable lock member which is moveable between a first position in which the slidable lock member engages with an engagement portion of the adjustable force means to lock the adjustable force means at a position corresponding to the desired adjustment, thereby preventing unintentional adjustment of the adjustable force means, and a second position in which the slidable lock member is disengaged with the engagement portion of the adjustable force means, thereby unlocking the adjustable force means to permit adjustment.

2. An apparatus according to claim 1, wherein said valve permits adjustment of said desired value of the level of vacuum in the conduit, within a specific range.

3. An apparatus according to claim 1, wherein said adjustable force means includes an adjuster arranged to rotate relative to a body of the valve, and wherein the slidable lock member is arranged to engage with the adjuster and prevent adjustment once engaged therewith.

4. An apparatus according to claim 1, wherein the lock mechanism is releasable.

5. An apparatus according to claim 1, wherein the lock mechanism includes a one way lock which is not releasable once engaged.

6. An apparatus according to claim 4, wherein the lock mechanism is releasable by a separate release initiator.

7. An apparatus according to claim 1, wherein the slidable lock member includes at least one latch member arranged to slidably engage with the at least one engagement portions on the force adjustment means.

8. An apparatus according to claim 1, wherein the adjustable force means includes a rotatable member.

9. An apparatus according to claim 8, wherein the rotatable member includes one or more engagement portions around a periphery thereof and the slidable lock member engages with one or more of the engagement portions at a selected position of rotation of the rotatable member.

10. An apparatus according to claim 1, wherein the lock mechanism includes a ratchet mechanism providing a one way locking adjustment or a releasable lock.

11. An apparatus according to claim 10, the ratchet mechanism including one or more ratchet members engaging into one or more respective ratchet recesses or teeth.

12. An apparatus according to claim 11, wherein the ratchet member(s) is/are provided on the adjustable force means and the ratchet recess(es) or teeth on a corresponding portion of the valve fixed relative to the adjustable force means.

13. An apparatus according to claim 12, wherein, where the adjustable force means includes a rotatable member, the rotatable member includes a series of ratchet teeth or recesses around at least a part of a periphery thereof, those ratchet teeth or recesses arranged to selectively engage with a resilient member on a fixed portion of the valve.

14. A wound drainage device provided as a kit of parts including container for receiving fluid to be drained from a wound, conduit for providing a flow passage from the wound to a flow control apparatus, a conduit providing a flow passage from the flow control apparatus to the container, and a flow control apparatus according to claim 1.

15. An apparatus according to claim 1, wherein the slidable lock member is removably coupled to the cover.

16. A wound drainage device flow control apparatus, the wound drainage device for withdrawing fluid from a wound comprising a conduit to be connected at one end to a wound to receive fluid from the wound and to deliver said fluid to a container, the flow control apparatus, in use, to selectively provide communication between the conduit and container, comprising a valve arranged to establish communication between the conduit and the container in response to a level of vacuum in said conduit below a selected value, the valve including a diaphragm exposed to atmospheric pressure on one side and to the level of vacuum in the conduit on the other side, and an adjustable force means arranged to apply a force to the diaphragm in opposition to the atmospheric pressure, the difference between the force applied by the adjustable force means and the force generated by the atmospheric pressure providing a control force required to be applied by the level of vacuum in the conduit to close the valve to interrupt communication between the container and the conduit, and a lock mechanism arranged to lock the adjustable force means at a desired adjustment corresponding to a desired level of vacuum, whereby the lock mechanism includes a slidable lock member which is moveable between a first position in which the lock member engages with an engagement portion of the adjustable force means to lock the adjustable force means at a position corresponding to the desired adjustment, thereby preventing unintentional adjustment of the adjustable force means; and a second position in which the lock member is disengaged with the engagement portion of the adjustable force means, thereby unlocking the adjustable force means to permit adjustment.

* * * * *